United States Patent [19]

Liu

[11] Patent Number: 5,834,605

[45] Date of Patent: Nov. 10, 1998

[54] SAFE PHARMACEUTICAL COMPOSITION FOR TREATING AND PREVENTING ALCOHOL ABUSE AND INCREASING IMMUNE FUNCTION

[76] Inventor: Yaguang Liu, 67-08 168th St., Flushing, N.Y. 11365

[21] Appl. No.: 888,536

[22] Filed: Jul. 7, 1997

[51] Int. Cl.$^6$ ............................. C07H 15/00; A01N 65/00
[52] U.S. Cl. ............................. 536/8; 424/195.1; 514/456; 549/403
[58] Field of Search ........................ 549/403; 424/195.1; 536/8; 514/456

[56] References Cited

U.S. PATENT DOCUMENTS

| | | | |
|---|---|---|---|
| 5,516,528 | 5/1996 | Hughes et al. | 424/464 |
| 5,523,087 | 6/1996 | Shlyankevich | 424/195.1 |
| 5,637,561 | 6/1997 | Shen et al. | 514/2 |
| 5,639,785 | 6/1997 | Kung | 514/456 |
| 5,679,806 | 10/1997 | Zheng et al. | 549/403 |
| 5,726,034 | 3/1998 | Bryan et al. | 435/68.1 |

*Primary Examiner*—Herbert J. Lilling

[57] ABSTRACT

The safe pharmaceutical composition and processed are provided for treating and preventing alcohol abuse and increasing immune function. The pharmaceutical composition is composed of Puerarin derivatives, which includes Puerarin, Daidzein or Genistia.

2 Claims, No Drawings

SAFE PHARMACEUTICAL COMPOSITION FOR TREATING AND PREVENTING ALCOHOL ABUSE AND INCREASING IMMUNE FUNCTION

BACKGROUND OF THE INVENTION

This invention relates to a safe and natural pharmaceutical composition for treating and preventing alcohol abuse and increasing immune function contains Puerarin derivatives. The processes for producing Puerarin derivatives and related pharmacological effect are provided.

DESCRIPTION OF PRIOR ART

Alcohol abuse (alcoholism) is a major medical and public health problem in many societies. About 10% of all deaths in the United States may be directly alcohol-related. Alcohol abuse leads to increase risk especially by motor vehicle and fire and other accidents. Alcohol abuse is also leads work and family problems and associated with brain damage, cancer, heart attacks and high blood pressure.

Antabuse (disulfiram) and tranquilizers are sometimes used for treating alcohol abuse. However, they are neither an instant solution to the problems of alcoholism, nor a complete therapy. Also, they have side effects.

Pueraria DC, includes Pueraria lobata (willd.) Ohwi, Pueraria thomsanni Benth, Pueraria thundergiana, Pueraria edulis Pamp, et al., is used for treating cardiovascular disease and alcohol abuse. U.S. Pat. No. 4,985,431 disclosed that Pueraria was extracted from roots of Pueraria DC and they used for treating and preventing cardiovascular disease. Pueraria DC is used for treating of alcohol abuse in China for long time. However, according to traditional Chinese medical way, the whole plant or root, flower and seed of plants were put into a bowl of water boiling nearby, then patients drank above liquid. This way, obviously, cannot be industrialize. In this invention, Pueraria DC is extracted by plant biochemistry and obtained active ingredients. Further, the chemical structure of ingredient has been indicated. It is important that patients with alcohol abuse have lower immune function which will cause more diseases. So far, there is no effective and safe drugs which can be treated and prevented alcohol abuse and increased immune function without side effects.

DETAILED DESCRIPTION

The present invention provides a safe and natural pharmaceutical composition which is high effective for treating and preventing alcohol abuse. These objects and other objects will become apparent hereinafter, after reading the detailed discription in conjunction with the examples the present invention resides, briefly stated in compositions comprising Puerarin derivatives.

Extracts of root and flower or whole plant of Pueraria DC have a lot of ingredients, at least having more than ten ingredients, are extracted. The major part of ingredients, however, have no pharmaceutical function. Only few ingredients, in special, Puerarin derivatives can strongly treat and prevent alcohol abuse. More important, the structures of many ingredients of Puearia's extract have not been indicated. On the contrary, the chemical structure of Puerarin derivatives has been indicated. If the extracts of Pueraria or other plants do not have chemical structure and definite chemical and physical index, the quality and quantity of the extracts cannot be identified, and they cannot be industrialized. For the reason given above, traditional oriental medicine and many present herb's products, which include crude extracts of herbs, cannot be industrialized and they cannot be approved by Food and Drug Administration of U.S.A. (FDA).

For the sake of convenience, pharmaceutical compositions comprising Puerarin derivatives which used for treating and preventing alcohol abuse will hereinafter be refereed to as "PTA".

PTA can be administered to patients in the form of capsules containing a powdered of the active ingredients. Alternatively, tablets can be prepared comprising the active ingredients and pharmaceutical acceptable binders, excipiebts, lubricants, sweeteners and coatings. A syrup or elixir may be prepared by dissolving PTA in alcohol or water together with suitable preservatives, sweeteners, dyes and flavoring agents. Ampules may likewise be prepared, with the PTA as prepared for oral administration being purified through further purification and sterilization and the addition thereto of distilled water and other suitable solvents and additives known in the pharmaceutical art.

The PTA dosage units prepared according to the invention can be administered to patients. PTA is nontoxic.

Puerarin derivatives has the following structure of formula.

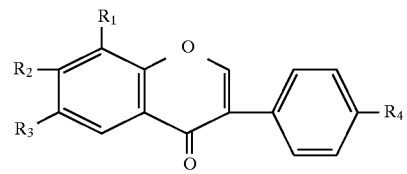

$R_1$=H, OH, Glucose;
$R_2$=H, OH, Glucose, OGlc, OMe, OAc and Cl;
$R_3$=H, OH, 2-0-(6-Deoxy-α-L-mannopyranosyl)-β-D-glucopyranosyloxy;
$R_4$=H, OH, Glucose.

When $R_1$=Glucose, $R_2$=OH, $R_3$=OH, $R_4$=H, it is Puerarin.
When $R_1$=H, $R_2$=OGlc, $R_3$=H, $R_4$=OH, it is Daidzin.
When $R_1$=H, $R_2$=OH, $R_3$=H, $R_4$=OH, it is Daidzein.
When $R_1$=OH, $R_2$=H, $R_3$=2-0-(6-Deoxy-α-L-mannopyranosyl)-β-D-glucopyranosyloxy, $R_4$=OH, it is Naringin.
When $R_1$=OH, $R_2$=H, $R_3$=OH, $R_4$=OH, it is Naringenin.
When $R_1$=H, $R_2$=OGlu, $R_3$=H, $R_4$=OH, it is Genistin.

The following specific examples will provide detailed illustrations of methods of producing PTA according to the present invention and pharmaceutical dosage units containing PTA. Moreover, examples will be given of pharmaceutical testing performed with PTA which demonstrates its effectiveness in treating and preventing alcohol abuse effects and increasing immune function. These examples are not intended, however, to limit or restrict the scope of the invention in any way, and should not be construed as providing conditions, parameter, reagents, or starting materials which must be utilized exclusively in order to practice the present invention.

EXAMPLE 1

Extraction of Daidzin

Daidzin is one of Puerarin derivatives. Daidzin was extracted from seed of Glycine maxl, Leguminosae (soybean) or Pueraria lobata (willd.) Ohwi.

The seed of soybean dried and powdered. One kilogram (1 kg) of powder was dipped in 5 liters 95% ethanol. It repeated twice with fresh 95% ethanol. Extract combined. Extract was concentrated to syrup under reduced pressure and ethanol was recovered. Syrup dry at 70° C. Drying-syrup was chromatographed on alumina using water-saturated butanol as the developing solvent to separate into color bands which were checked under ultraviolet light (U.V.). Special violeband ( $$UV\lambda_{Max}^{MeOH}$$

nm 230, 260) was cut and using butanol-pyridine as the developing solvent systems. Butanol-pyridine was recovered under vacuum distillation to yield crystals. Recrystallization from ethanol. The final product was Daidzin (m.p. 254° C.).

In general, daidzin was extracted from R. Puerariae and rosaceae, hasegawa or podocarpus spicata. But above plants are more expensive and its resources are poor. The present invention provides a method which can extract Daidzin from soybean. Soybean is very cheap. The resource of soybean is very huge in the U.S. and the world. Therefore, present invention provides a very cheap and industrial method for manufacturing daidzin.

EXAMPLE 2

Extraction of Genistin

Genistin is one of Puerarin derivatives. Genistin was extracted from seed of Glycine max (L.) Merr. (soybean). or Pueraria DC.

1 kg dried ground powder of seed of soybean extracted with 10 L of methanol for 12 hours. To repeat twice with fresh 5 L methanol. Extract combined with methanol were recovered under vacuum distillation and the residue obtained and dissolved in 500 ml of benzene. Benzene was recovered under vacuum distillation. Residue was chromatography on alumina and using benzene as the developing solvent to separate into violet. Bond having ( $$UV\lambda_{Max}^{MeOH}$$

nM: 260, 330) was cut and using benzene as the developing. Under vacuum distillation yellow crystals were obtained and mother solution was concentrated continuously. Yellow slices were crystallized. Recrystalized. The yellow crystallizes were Genistin (m.p. is 256° C.).

In general, genistin was extracted from R. Puerariae and rosaceae, hasegawa or podocarpus spicata. But above plants are more expensive and its resources are poor. The present invention provides a method which can extract Genistin from soybean. Soybean is very cheap. The resource of soybean is very huge in the U.S. and the world. Therefore, present invention provides a very cheap and industrial method for manufacturing Genistin.

EXAMPLE 4

Radioimmunoassays for the quantitative Determination of Puerarin Derivatives Quantitative determination of Puerarin derivatives (PD) is important for manufacturing Pueraria derivatives. Also, micro-determination of PD is more important for using PD in treating alcohol abuse. In special, patient with alcohol abuse has a high alcohol. Therefore, when dosage of drug is higher, excess Puerarin derivatives which dissolve in blood alcohol can cause side effects. So far, thin chromatography is used for quantitative determination of PD. Thin chromatography, however, is very crude method. Statistical errors of analytical data of thin chromatography are too large. Therefore, it has no any precise methods for determination concentration of Puerarin derivatives in human blood now. Above situation interferes Puerarin derivatives used for clinic. The present invention proved microdetermination of PD. It is Radioimmunoassays (RIA). RIA allows the rapid, sensitive and precise determination of PD in blood and other place. For example, RIA allows measuring range from 5 to 100 ng ($10^{-9}$ g) for PD, including daidzin, genistin and puerarin.

[$^3$H]-Daidzein, [$^3$H]-Genistin or [$^3$H]-Pueraria and antiserum production are prepared as general methods. RIA is performed as the following: Triplicate determinations are performed throughout. Glass tubes received 0.1 ml diluted sample, 0.5 ml incubation buffer, 0.1 ml 1:6 diluted bovine serum and 0.1 ml diluted tracer (about 15,000 CPM). The incubation was started by the addition of diluted antiserum with subsequent mixing. The samples were incubated at room temperature for 1 hour followed by the addition of 1 ml 90% $(NH_2)_4SO_4$ and mixing. The samples were further incubated for 1 hour at room temperature and then centrifuged (10 minuted, 5000 rpm). The pellets were washed with 1 ml 45% $(NH_2)_4SO_4$. Dissolved in 0.5 ml of $H_2O$ and mixed with 1 ml of scintillation fluid. The tubes were counted for radioactivity. Calculations were done by spline approximation for standard curve construction.

EXAMPLE 4

Effect of Drug on Alcohol Concentration of Blood

Male mice between 20–24 g were used in this study. The mice were treated with alcohol or saline. On the injection day alcohol was diluted with sterile saline to 35% (V/V) and mice were injected with the concentration of 4 g/kg body weight. Mice of treatment group were injected with drug and mice of control group were injected with saline. Mice were sacrificed by decapitation at various time point after treatment. Blood samples were collected for the determination of alcohol and other biochemical index.

TABLE 1

| | Alcohol concentration (m. mol/l) | | | | |
|---|---|---|---|---|---|
| | 1 hr. | 2 hr. | 4 hr. | 8 hr. | 24 hr. |
| Control group | 40.2 ± 3.4 | 35.2 ± 3.1 | 30 ± 2.0 | 25 ± 2.0 | 10.2 ± 1.8 |
| DA | *23.6 ± 3.1 | *21.2 ± 2.0 | **19.7 ± 1.5 | *15.2 ± 1.3 | 6.1 ± 0.7 |
| GE | *24.8 ± 2.9 | *20.9 ± 2.1 | *18.0 ± 2.0 | *16.4 ± 1.9 | 5.0 ± 0.4 |
| PN | *24.5 ± 2.5 | *22.2 ± 2.3 | *19.1 ± 2.1 | *16.2 ± 2.0 | 6.3 ± 0.4 |
| DA + GE | **20.1 ± 2.0 | **18.6 ± 1.9 | **16.3 ± 1.4 | **12.6 ± 1.5 | 4.2 ± 3.8 |

*$P < 0.05$, **$P < 0.01$, Statistical analysis was performed

*P<0.05, ** P<0.01, Statistical analysis was performed with the alcohol concentration, and P value expressed for drug-treated against saline-treated rate. PN: Puerarin (10 mg/kg), DA: Daidzin (10 mg/kg), GE: Genistin (10 mg/kg), DA+GE: DA (5 mg/kg)+GE (5 mg/kg).

Above data indicated that drugs strongly decreased the alcohol concentration in blood. DA+GE group is more effective decreasing alcohol than one drug used alone.

EXAMPLE 5

Effects of Drug on Certain Enzymes Related to Alcohol Metabolism of Rat Liver

The main pathway for alcohol metabolism involved alcohol dehydrogenase, an enayme catalyzts the conversion of alcohol to acetaldehyde. Drugs were significantly increasing in the activities of alcohol dehydrogenase (ADH) and acetaldehyde dehydrogenase (ALDH). The method of animal was same as example 4. After drug treated 6 hours, ADH and ALDH of rat liver were determined.

TABLE 2

|  | ADH mU/mg of protein | ALDH mU/mg of protein |
| --- | --- | --- |
| Control group | 8.70 ± 0.68 | 14.8 ± 1.5 |
| DA | *17.5 ± 1.8 | *25.6 ± 2.0 |
| GE | *18.2 ± 2.1 | *24.7 ± 2.8 |
| PN | *16.5 ± 2.0 | *23.8 ± 2.6 |
| DA + GE | **24.6 ± 2.2 | **30.8 ± 3.2 |

*P < 0.05, **P < 0.01

Table 2 shows that the use of drug significantly increases actively of ADH and ALDH and alcohol metabolizm. DA+GE group is more effectively than one drug used alone.

EXAMPLE 6

Effects of Drug on Alcohol Concentration in Human Blood

The 40 men had mean (±SD) age at the time of test of 50.6±3.86 years.

Control and treatment group were similar on height-to-weight. On the average drinking day. Every man drank 2.0 g of alcohol per kg of body weight. Then men of treatment group drank 100 ml of daidzin which contained 5 mg DA/kg body weight and men of control group drank 100 ml water. Blood samples were collected for the determination of alcohol concentration at each time point.

TABLE 3

Blood alcohol concentration in gm/dl after alcohol administration in 20 men

| Time post-alcohol administration | control (20 men) mean (± SD) | Treatment (20 men) mean (± SD) | P |
| --- | --- | --- | --- |
| 30 min | 0.072 ± 0.010 | 0.051 ± 0.090 | <0.01 |
| 1 hr. | 0.093 ± 0.015 | 0.062 ± 0.095 | <0.01 |
| 2 hr. | 0.060 ± 0.011 | 0.032 ± 0.091 | <0.01 |
| 4 hr. | 0.0370 ± 0.009 | 0.011 ± 0.050 | <0.05 |
| 8 hr. | 0.0120 ± 0.008 | 0.0040 ± 0.001 | <0.01 |

Data of Table 3 indicated that drug is very significantly decreasing the alcohol concentration in blood of men.

EXAMPLE 7

Effects of Drug on Immune Function of Alcohol Abuse, Experiment of Animal is same as Example 4

Methods of lymphoblastoid transformation test are described as follows.

I. Reagents and conditions for cell culture
   a. Culture media-RPMI 1640, medium 199 minimal essential medium (Eagle).
   b. 37° C. to maintain the pH of the medium at 7.3.
   c. Serum-generally 15–20% fetal bovine serum was incorporated, for lymphocytes from mice, 5% was used.
   d. Gaseous phase 5% $CO_2$ in air.
   e. Cell concentration-generally $1–2\times10^6$/ml.
   f. Stimulants: 20 µl/ml for phytoagglutinin containing polysaccaride-free purified phytoagglutinin (PHA-P).
II. Measure by liquid scintillation
   a. The conditions of cell culture were same as above. $^3$H-TdR, was added after 48 hours of incubation at a final concentration of 2 µCi/ml and continue the incubation for 24 hours.
   b. Wash the cells twice with cold normal saline and the erythrocytes were lysed by addition of distilled-water and equal volume of 3.6% NaCl was then added. The intact lymphocytes were again washed once with cold saline. Spin down the lymphocytes and add 2 ml of 10% trichloroacetic acid to precipitate the protein. Wash twice with normal saline. Add 2 ml of formic acid was then added for digestion till the precipitate was dissolved.
   c. Add 4 ml of scintillation fluid to 0.1 ml of the final sample and count in a liquid scintillation counter.

Results are listed in the following table 4.

TABLE 4

Effects of drug on lymphoblastoid transformation

|  | Normal | Alcohol abuse group | Alcohol abuse + DA | alcohol abuse + GE |
| --- | --- | --- | --- | --- |
| CPM | 1450 ± 188 | 805 ± 142 | 1380 ± 140 | 1308 ± 120 |
| Number of sample | 10 | 10 | 10 | 10 |
| P |  | <0.01 |  |  |

Examination of the immune function showed a significantly decreasing in lymphoblastoid transformation of alcohol abuse group. Meanwhile, DA and GE induced a significant increasing in the lymphoblastoid transformation.

The preparation of PD is simple and can be accomplished by the extraction methods set forth above or any conventional methods for extracting the active ingredients from the plant tissues. The novelty of the present invention resides in the PD or in the specified proportions to produce DA and GE in the preparation of dosage units in pharmaceutically acceptable dosage form. The term "pharmaceutically acceptable dosage form" as used hereinabove includes any suitable vehicle for the administration of medications known in the pharmaceutical art, including, by way of example, tablets, capsules, syrups, elixirs, and solutions for parenteral injection with specified ranges of PD concentration. The present invention provides novel methods for treating and preventing alcohol abuse with easily produced, safe pharmaceutical agent.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims:

1. A process for producing a pharmaceutical composition of Daidzin for alcohol abuse comprising:
   (a) extracting powder of Pueraria or seed of soybean with 95% ethanol and recovering extract;
   (b) concentrating the extract by vacuum distillation and residue is obtained;
   (c) residue was chromatography on alumina using water-saturated butanol as the developing solvent(1);
   (d) charomatographic separation was made, using a UV absorption detector; separation with special violetband from 230 to 310 nM was cut and using butanol-pyridine as developing solvent (2) systems;
   (e) the developing solvent(2) of butanol-pyridine was collected and recovered under vacuum distillation to yield crystal;
   (f) recrystalization from ethanol; and
   (g) the final product is Daidzin.

2. A process for producing a pharmaceutical composition of Genistin for alcohol abuse comprising:
   (a) extracting powder of Pueraria or seed of soybean with methanol and recovering extract(1);
   (b) concentrating the extract(1) by vacuum distillation;
   (c) the extract(1) of methanol is recovered and a still residue(1) is obtained, this still residue(1) dissolved in benzene and extract(2) is obtained;
   (d) concentrating the extract(2) of benzene by vacuum distillation and the residue(2) is obtained;
   (e) the residue(2) was chromatography on alumina using benzene as the developing solvent(1);
   (f) charomatographic separation was made, using a UV absorption detector; separation with special violetband from 230 to 260 nM was cut and using benzene as the developing solvent(2);
   (g) the developing solvent(2) of benzene was recovered under vacuum distillation to yield yellow crystals and mother solution;
   (h) mother solution was concentrated continuously to yield yellow crystals;
   (i) recrystalization from benzene; and
   (j) the final product is Genistin.

* * * * *